United States Patent [19]

Pomerantz

[11] 4,337,745

[45] Jul. 6, 1982

[54] CLOSED LOOP AIR/FUEL RATIO CONTROL SYSTEM WITH OXYGEN SENSOR SIGNAL COMPENSATION

[75] Inventor: Allen J. Pomerantz, Bancroft, Mich.

[73] Assignee: General Motors Corporation, Detroit, Mich.

[21] Appl. No.: 191,070

[22] Filed: Sep. 26, 1980

[51] Int. Cl.³ ............................................. F02M 7/00
[52] U.S. Cl. ..................................... 123/440; 123/489
[58] Field of Search .................... 123/489, 440; 73/23; 204/195 S

[56] References Cited

U.S. PATENT DOCUMENTS

| | | | |
|---|---|---|---|
| 4,191,151 | 3/1980 | Wanamaker | 123/440 |
| 4,224,913 | 9/1980 | Barnard | 123/440 |
| 4,228,775 | 10/1980 | Schweikert | 123/440 |
| 4,258,563 | 3/1981 | Yasuda et al. | 123/489 |
| 4,274,381 | 6/1981 | Abo | 123/489 |

*Primary Examiner*—P. S. Lall
*Attorney, Agent, or Firm*—Howard N. Conkey

[57] ABSTRACT

The signal provided by an oxygen sensor monitoring the exhaust discharge from an internal combustion engine having a closed loop air/fuel ratio controller is compensated so that the controller is insensitive to the difference between the rich-to-lean and lean-to-rich time responses of the sensor signal. The compensated sensor signal has fixed symmetrical voltage change slopes which are set at a value smaller than the smallest of the two slopes of the sensor signal when the compensated sensor signal being clamped at rich and lean voltages that are respectively less than and greater than the sensor rich and lean voltages.

2 Claims, 9 Drawing Figures

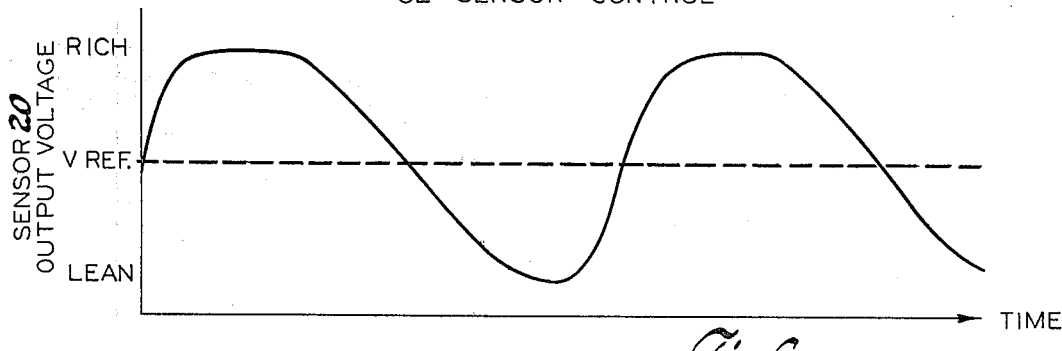
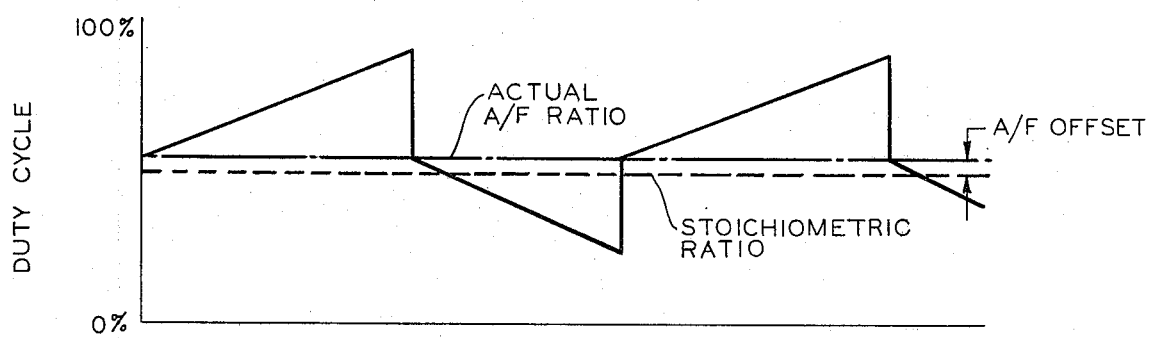
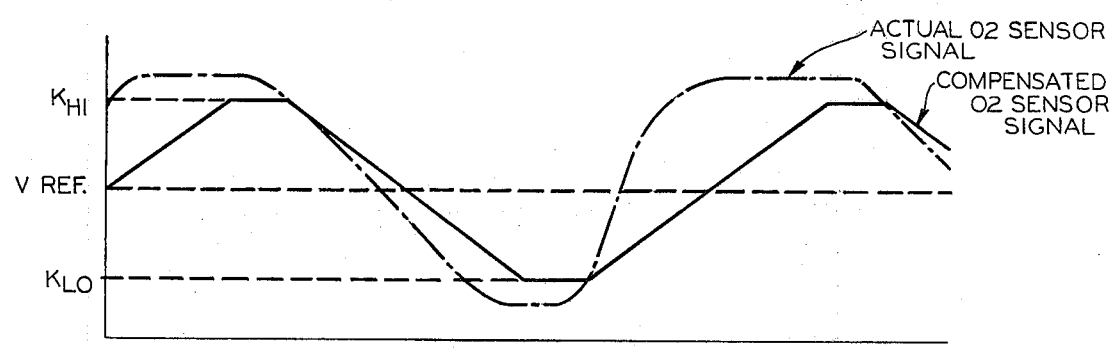
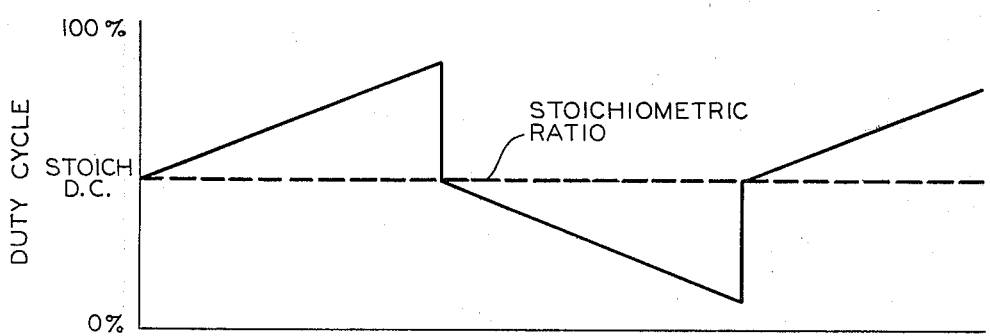

CLOSED LOOP AIR/FUEL RATIO CONTROL SYSTEM WITH OXYGEN SENSOR SIGNAL COMPENSATION

This invention is directed toward a closed loop air/fuel ratio mixture controller for an internal combustion engine employing a sensor exposed to the exhaust gas discharge of the engine.

A single catalytic device may be utilized to accomplish both the oxidation and reduction necessary for minimizing the undesirable exhaust components discharged from an internal combustion engine provided that the air/fuel mixture supplied to the engine is maintained within a narrow band near the stoichiometric ratio. A closed loop controller is generally employed to maintain the mixture of the gases supplied to the converter within this narrow band. The most common forms of these closed loop systems respond to a sensor that monitors the oxidizing/reducing conditions in the exhaust gases and provides a control signal for adjusting the air/fuel ratio of the mixture supplied to the engine. These systems commonly employ a zirconium oxygen sensor which provides an output signal that shifts rather abruptly between two voltage levels with small changes in the air/fuel ratio around the stoichiometric ratio.

The zirconia oxygen sensor provides an output signal at a high voltage level when the air/fuel ratio of the mixture supplied to the internal combustion engine is less than the stoichiometric ratio and provides a relatively low level voltage signal when the air/fuel ratio of the mixture supplied to the internal combustion engine is greater than the stoichiometric ratio. However, these sensors are generally affected by such parameters as temperature, age and contamination. For example, the zirconia sensor is characterized in that its time response to changing oxidizing/reducing conditions in a first direction through the stoichiometric ratio varies from its time response to changing oxidizing/reducing conditions in the opposite direction through the stoichiometric ratio. Typically, the time response of the zirconia sensor to air/fuel ratios varying from a ratio greater than the stoichiometric ratio to a ratio less than the stoichiometric ratio is faster than the time response when the air/fuel ratio varies from a value less than the stoichiometric ratio to a value greater than the stoichiometric ratio. In addition, the sensor time response may vary with sensor use.

The aforementioned sensor characteristic may affect the operation of the closed loop controller in its ability to maintain the air/fuel ratio at the desired value such as the stoichiometric ratio. For example, it is usual to provide a comparator switch which compares the amplitude of the output signal from the zirconia sensor with a constant reference level having a value generally between the maximum and minimum values of the output signal and which provides a two-level signal which represents the sense of deviation of the oxidizing/reducing conditions from the stoichiometric condition. However, in these systems, the aforementioned sensor characteristic may result in the closed loop controller adjusting the air/fuel ratio of the mixture supplied to the engine to a value offset from the desired value thereby affecting the efficiency of the three-way catalytic device relative to at least one undesirable exhaust gas constituent.

It is the general object of this invention to provide an improved air/fuel ratio controller in which the output of the exhaust gas sensor is compensated so as to provide a compensated sensor signal that is substantially independent of certain sensor characteristics.

It is another object of this invention to provide for a closed loop air/fuel ratio controller for an internal combustion engine in which the output signal from a sensor sensing the oxidizing/reducing conditions in the exhaust gases of the internal combustion engine is compensated to provide a compensated sensor signal that is substantially independent of the sensor time response characteristics.

It is another object of this invention to provide a compensated exhaust gas sensor signal in a closed loop air/fuel ratio controller that may be compared with a single constant reference signal to provide air/fuel ratio adjustments that are independent of the exhaust gas sensor time response characteristics.

These and other objects of this invention may be best understood by reference to the following description of a preferred embodiment and the drawings in which.

Figure 1:
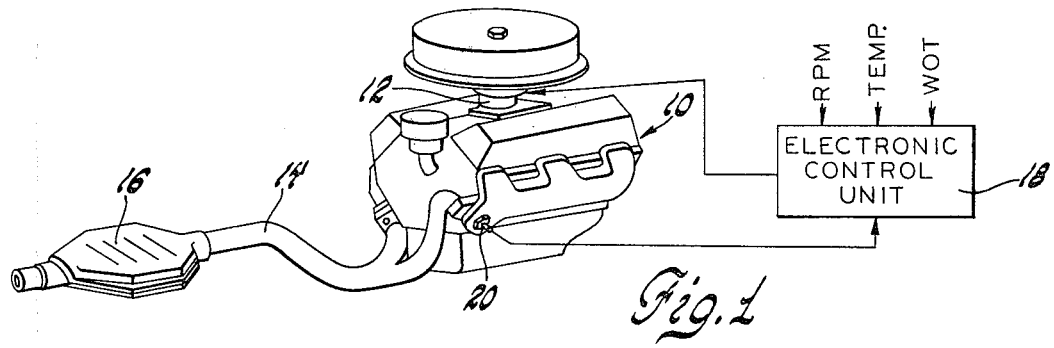
FIG. 1 illustrates an internal combustion engine incorporating a closed loop air/fuel ratio control system employing the principles of this invention.
Figure 2:
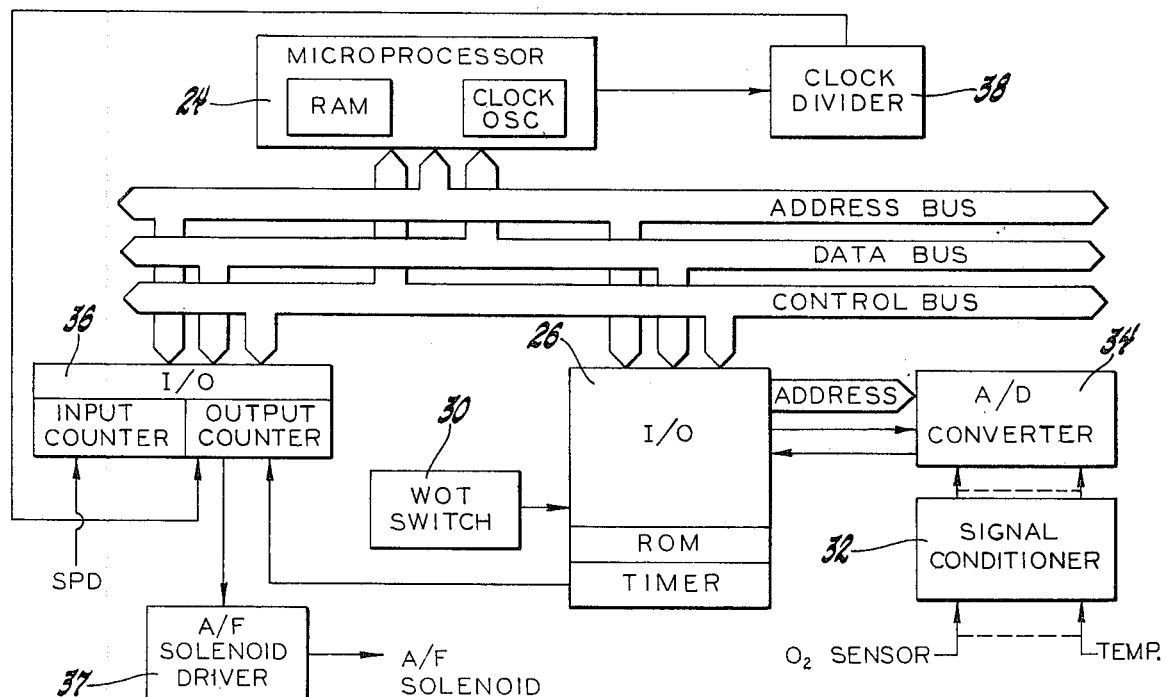
FIG. 2 illustrates a digital controller for controlling the air and fuel mixture supplied to the engine of FIG. 1 in accord with the principles of this invention.
Figure 3:
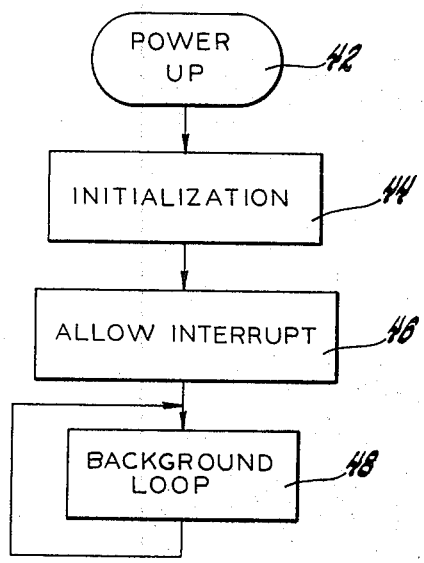
Figure 4:
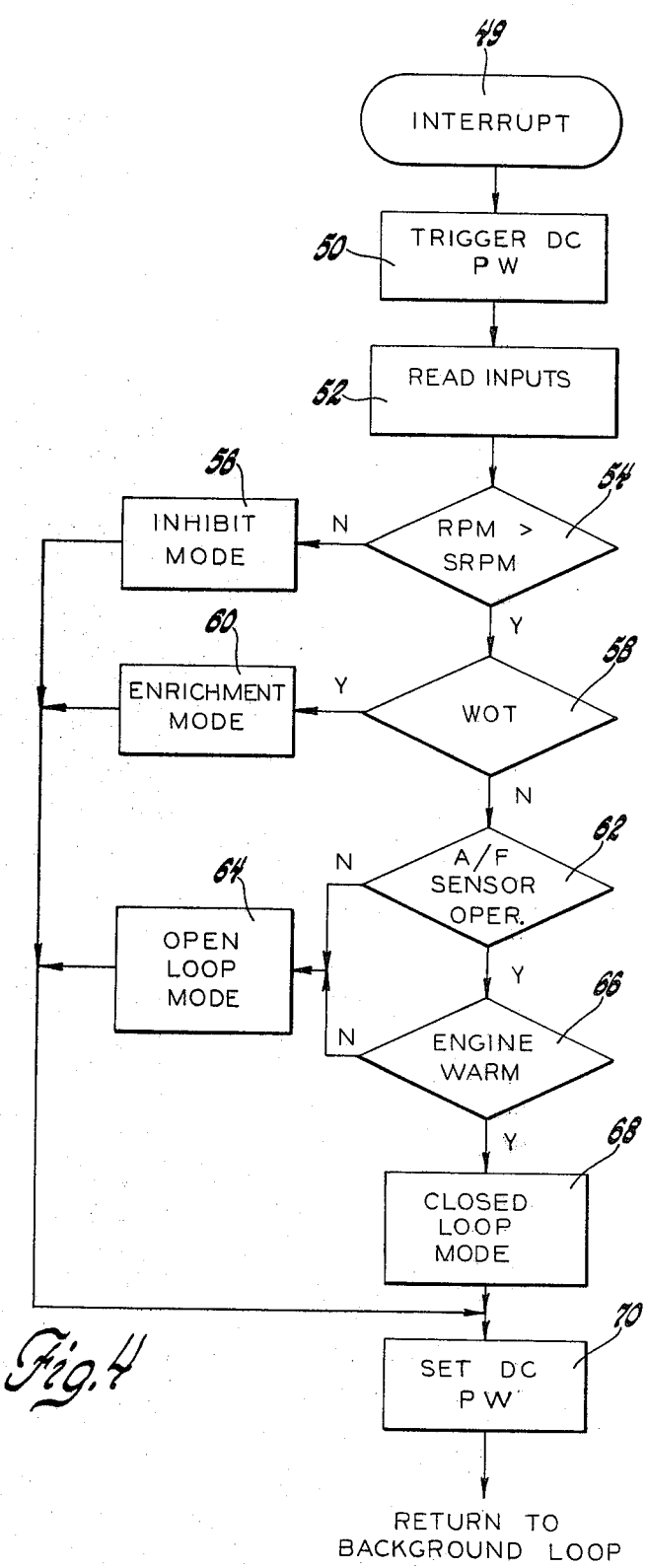
Figure 5:
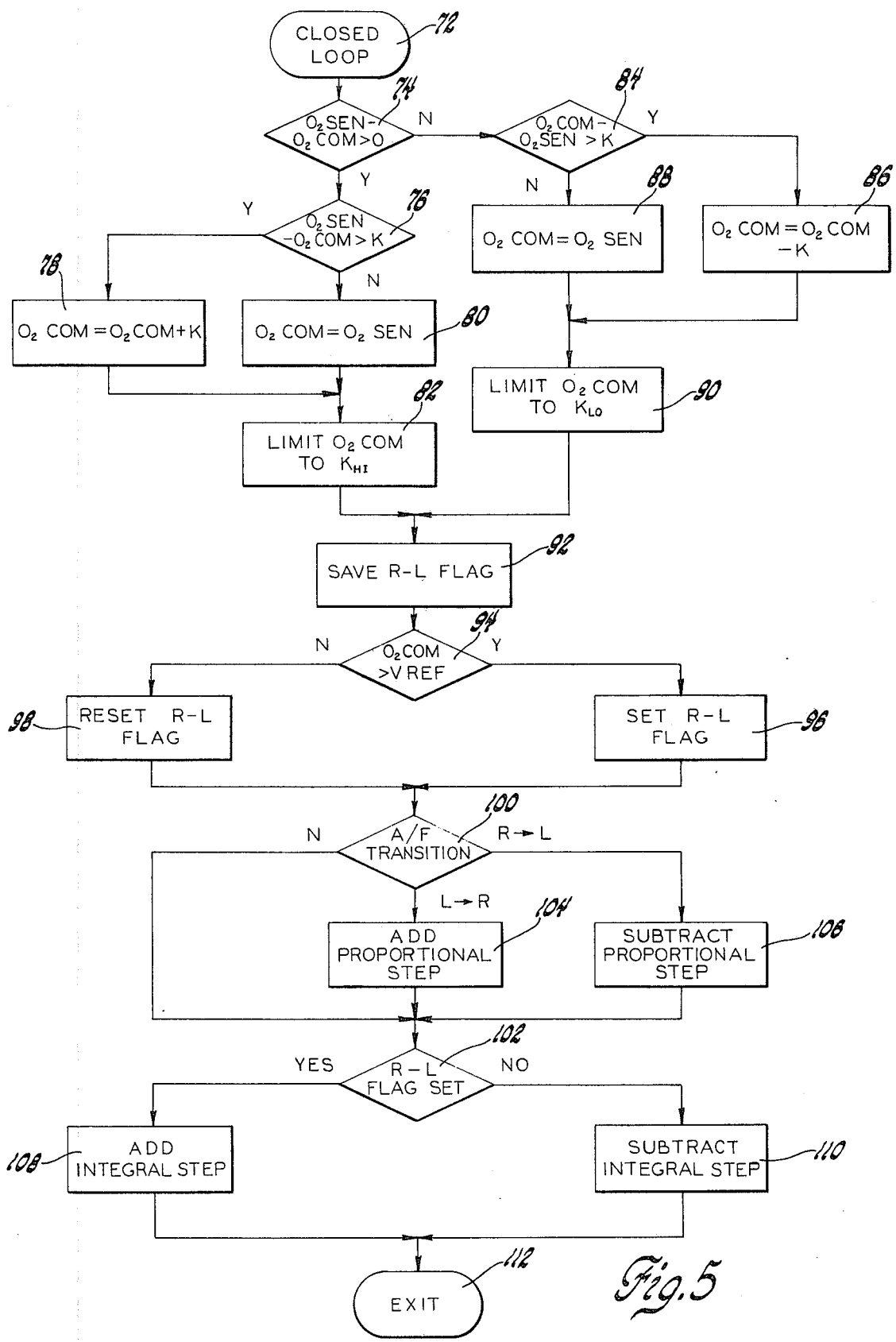

FIGS. 3, 4 and 5 are diagrams illustrative of the operation of the digital controller of FIG. 2 so as to provide adjustment of the air/fuel ratio of the mixture supplied to the engine of FIG. 1 substantially independent of the time response characteristics of the sensor signal in accord with the principles of this invention; and FIGS. 6a thru 6d are graphs illustrating the operation of a conventional air/fuel ratio controller and the air/fuel ratio controller employing the principles of this invention.

Referring to FIG. 1, an internal combustion engine 10 is supplied with a controlled mixture of fuel and air by a carburetor 12. The combustion byproducts from the engine 10 are exhausted to the atmosphere through an exhaust conduit 14 which includes a three-way catalytic converter 16. The catalytic converter 16 simultaneously converts carbon monoxide, hydrocarbons and nitrogen oxides with maximum three-way conversion if the air/fuel mixture supplied thereto is maintained near the stoichiometric value.

The air/fuel ratio of the mixture supplied by the carburetor 12 is selectively controlled either open loop or closed loop by means of an electronic control unit 18. During open loop control, the electronic control unit 18 is responsive to predetermined engine operating parameters to generate an open loop control signal to adjust the air/fuel ratio of the mixture supplied by the carburetor in accord with a predetermined schedule. When the conditions exist for closed loop operation, the electronic control unit 18 is responsive to the output of an air/fuel ratio sensor 20 positioned at the discharge point of one of the exhaust manifolds of the engine 10 and which senses the exhaust discharge therefrom to generate a closed loop control signal for adjusting the carburetor 12 to obtain a predetermined air/fuel ratio such as the stoichiometric ratio. The sensor 20 is preferably of the zirconia type which generates an output voltage that achieves its maximum value when exposed to rich air/fuel mixtures and its minimum value when exposed to lean air/fuel mixtures.

The electronic control unit 18 receives inputs from other sensors including an engine speed sensor providing a speed signal RPM, an engine temperature sensor providing a temperature signal TEMP and a wide-open throttle switch providing a signal WOT when the throttle is in a wide-open position. These sensors are not illustrated and take the form of any of the well known sensors for providing signals representative of the values of the aforementioned parameters. In general, the electronic control unit 18 is responsive to these signals to provide for the open loop air/fuel ratio schedule and to provide selection between the open and closed loop operating modes of the control unit.

In the present embodiment, the control signal output of the electronic control unit 18 takes the form of a pulse width modulated signal at a constant frequency thereby forming a duty cycle modulated control signal. This signal is coupled to the carburetor 12 to effect the adjustment of the air/fuel ratio supplied by the fuel metering circuits therein. In this embodiment, a low duty cycle output of the electronic control unit 18 provides for an enrichment of the mixture supplied by the carburetor 12 while a high duty cycle value is effective to lean the mixture.

An example of a carburetor 12 with a controller responsive to a duty cycle signal for adjusting the mixture supplied by its fuel metering circuits is illustrated in the U.S. Pat. No. 4,178,332 which issued on Dec. 11, 1979, and which is assigned to the assignee of this invention. In this form of carburetor, the duty cycle modulated control signal is applied to a solenoid which adjusts elements in the fuel metering circuits to provide for the air/fuel ratio adjustment.

Referring to FIG. 2, the electronic control unit 18 in the present embodiment takes the form of a digital computer that outputs a pulse width modulated signal at a constant frequency to the carburetor 12 to effect adjustment of the air/fuel ratio. The electronic control unit 18 determines the required pulse width during open loop operation in accord with a predetermined schedule in response to measured engine operating parameters and determines the pusle width during closed loop operation in response to the oxidizing/reducing conditions in the exhaust gases as sensed by the sensor 20.

The digital system includes a microprocessor 24 that controls the operation of the carburetor 12 by executing an operating program stored in an external read only memory (ROM). The microprocessor 24 may take the form of a combination module which includes a random access memory (RAM) and a clock oscillator in addition to the conventional counters, registers, accumulators, flag flip flops, etc., such as a Motorola Microprocessor MC-6802. Alternatively, the microprocessor 24 may take the form of a microprocessor utilizing an external RAM and clock oscillator.

The microprocessor 24 controls the carburetor 12 by executing an operating program stored in a ROM section of a combination module 26. The combination module 26 also includes an input/output interface and a programmable timer. The combination module 26 may take the form of a Motorola MC-6846 combination module. Alternatively, the digital system may include separate input/output interface modules in addition to an external ROM and timer.

The input conditions upon which open loop and closed loop control of air/fuel ratio are based are provided to the input/output interface of the combination circuit 26. The discrete inputs such as the output of a wide-open throttle switch 30 are coupled to discrete inputs of the input/output interface of the combination circuit 26. The analog signals including the air/fuel ratio signal from the sensor 20 and the engine temperature signal TEMP are provided to a signal conditioner 32 whose outputs are coupled to an analog-to-digital converter-multiplexer 34. The particular analog condition to be sampled and converted is controlled by the microprocessor 24 in accord with the operating program via the address lines from the input/output interface of the combination circuit 26. Upon command, the addressed condition is converted to digital form and supplied to the input/output interface of the combination circuit 26 and then stored in ROM designated locations in the RAM.

The duty cycle modulated output for controlling the air/fuel solenoid in the carburetor 12 is provided by an output counter section of an input/output interface circuit 36. The output pulses to the carburetor 12 are provided via a conventional solenoid driver circuit 37. The output counter section receives a clock signal from a clock divider 38 and a 10 hz signal from the timer section of the combination circuit 26. In general, the output counter section of the circuit 36 may include a register into which a binary number representative of the desired pulse width is inserted. Thereafter at frequency of the 10 hz signal from the timer section of the circuit 26, the number is gated into a down counter which is clocked by the output of the clock divider 38 with the output pulse of the output counter section having a duration equal to the time required for the down counter to be counted down to zero. In this respect, the output pulse may be provided by a flip flop that is set when the number in the register is gated into the down counter and reset by a carry signal from the down counter when the number is counted to zero.

The circuit 36 also includes an input counter section which receives the speed pulses from an engine speed transducer or the engine distributor that gate clock pulses to a counter to provide an indication of engine speed. While a single circuit 36 is illustrated as having an output counter section and an input counter section, each of those sections may take the form of separate independent circuits.

The microprocessor 24, the combination module 26 and the input/output interface circuit 36 are interconnected by an address bus, a data bus and a control bus. The microprocessor 24 accesses the various circuits and memory locations in the ROM and RAM via the address bus. Information is transmitted between circuits via the data bus and the control bus includes lines such as read/write lines, reset lines, clock lines, etc.

As previously indicated, the microprocessor 24 reads data and controls the operation of the carburetor 12 by execution of its operating program as provided in the ROM section of the combination circuit 26. Under control of the program, various input signals are read and stored in ROM designated locations in the RAM in the microprocessor 24 and the operations are performed for controlling the ratio of the air and fuel mixture supplied by the carburetor 12.

Referring to FIG. 3, when power is first applied to start the vehicle engine 10 and to apply power to the various circuits including the electronic control unit 18, the computer program is initiated at point 42 when power is first applied and proceeds to step 44. At this step, the computer provides for initialization of the system. For example, at this step, system initial values stored in the ROM are entered into ROM designated locations in the RAM in the microprocessor 24 and counters, flag flip flops and timers are initialized.

After the initialization step 44, the program proceeds to step 46 wherein the program allows interrupt routines to occur. For example, this may be accomplished by resetting the interrupt mask bit in the microprocessor condition code register. After step 46, the program shifts to a background loop 48 which is continuously repeated. The background loop 48 may include routines for controlling functions such as EGR and may also include diagnostic and warning routines.

While the system may employ numerous interrupts at various spaced intervals, it is assumed for purposes of illustrating this invention that a single interrupt routine is provided that is repeated each 100 milliseconds. During each 100 millisecond interrupt routine, the electronic control unit 18 determines the carburetor control pulse width in accord with the sensed engine operating conditions and issues a pulse to the carburetor solenoid driver 37. The 100 millisecond interrupt routine is initiated by the timer section of the combination circuit 26 which issues an interrupt signal at a 10 hz rate that interrupts the background loop routine 48. After each interrupt, the program enters the 100 millisecond interrupt routine at step 49 and proceeds to step 50 where the carburetor control pulse width in the register in the output counter section of the input/output circuit 36 is shifted into the output counter to initiate the generation of the carburetor control pulse as previously described. This pulse has a duration determined in accord with the engine operation to produce the duty cycle signal for adjusting carburetor 12 to obtain the desired air/fuel ratio of the mixture supplied to the engine 10.

The program then proceeds to step 52 where the computer executes a read routine. During this routine, the discrete inputs such as from the wide-open throttle switch 30 are stored in ROM designated memory locations in the RAM, the engine speed determined via the input counter section of the input/output circuit 36 is stored at a ROM designated memory location in the RAM and various inputs to the analog-to-digital converter including the engine temperature signal TEMP and the sensor 20 signal are one by one converted by the analog-to-digital converter-multiplexer 34 into a binary number representative of the analog signal value and stored in respective ROM designated memory locations in the RAM.

Following step 52, the program proceeds to a decision point 54 where the engine speed stored in the RAM at step 52 is read from the RAM and compared with a calibration reference engine speed value SRPM that is less than the engine idle speed, but greater than the cranking speed during engine start. If the engine speed is not greater than the reference speed SRPM, indicating the engine has not started, the program proceeds to an inhibit mode of operation at step 56 where the carburetor control pulse width for controlling the carburetor 12 and which is stored at a RAM location designated by the ROM to store the carburetor control pulse width is set essentially to zero thereby producing a zero percent duty cycle signal for setting the carburetor 12 to a rich setting to assist vehicle engine starting.

If the engine speed is greater than the reference speed SRPM indicating the engine is running, the program proceeds from the decision point 54 to a decision point 58 where it is determined whether or not the engine is operating at wide-open throttle thereby requiring power enrichment. This is accomplished by addressing and sampling the information stored in the ROM designated memory location in the RAM at which the condition of the wide-open throttle switch 30 was stored at step 52. If the engine is at wide-open throttle, the program proceeds to step 60 at which an enrichment routine is executed wherein the width of the carburetor control pulse width resulting in the duty cycle required to control the carburetor 12 for power enrichment is determined and stored in the RAM memory location designated to store the carburetor control pulse width.

If the engine is not at wide-open throttle, the program proceeds from the decision point 58 to the decision point 62 where it is determined if the air/fuel ratio sensor 20 is operational. In this respect, the system determines the operational status of the sensor 20 by the value of its temperature or impedance. If the air/fuel ratio sensor 20 is determined to be inoperative (high impedance or cold temperature) the program proceeds to the step 64 where an open loop mode routine is executed. During this mode, an open loop pulse width is determined in accord with input parameters such as engine temperature read and stored in the RAM at program step 52. The determined open loop pulse width is stored in the RAM location assigned to store the carburetor control pulse width.

If at decision point 62 the air-fuel sensor is determined to be operational, the program proceeds to the step 66 where the engine temperature stored in the RAM at step 52 is compared with a predetermined open loop to closed loop calibration value stored in the ROM. If the engine temperature is below this value, the program proceeds to the step 64 and executes the open loop routine previously described. If, however, at decision point 66 it is determined that the engine temperature is greater than the calibration value, all the conditions exist for closed loop operation and the program proceeds to step 68 where the closed loop routine is executed to determine the carburetor control signal pulse width in accord with the sensed air/fuel ratio. The determined closed loop pulse width is stored in the RAM location assigned to store the carburetor control pulse width.

From each of the program steps 56, 60, 64 and 68, the program cycle proceeds to a step 70 at which the carburetor control pulse width determined in the respective one of the operating modes is read from the RAM and entered in the form of a binary number into the register in the output counter section of the input/output circuit 36. This value is thereafter inserted into the down counter at step 50 during the next 100 millisecond interrupt period to initiate a pulse output to the air-fuel solenoid having the desired width. The carburetor control pulse is issued to energize the air/fuel ratio control solenoid in the carburetor 12 each 100 millisecond interrupt period so that the pulse width issued at a 10 hz frequency defines the variable duty cycle control signal for adjusting the carburetor 12.

As previously indicated, the voltage output of the sensor 20 achieves its maximum value with rich air-fuel mixtures and its minimum value with lean air-fuel mixtures. Further, the output voltage from the sensor 20 exhibits an abrupt change between the high and low voltage values as the air/fuel ratio of the mixture passes through the stoichiometric ratio.

The sensor 20 is generally characterized in that its time response to an air/fuel ratio varying from a value greater than the stoichiometric ratio to a value less than the stoichiometric ratio is faster than the time response to an air/fuel ratio varying from a value less than the stoichiometric ratio to a value greater than the stoichiometric ratio. Further, this difference in time response to changing air/fuel ratios in one direction from the time response to changing air/fuel ratios in the other direction varies as a function of ambient conditions such as temperature and sensor aging.

FIG. 6a illustrates the condition where the response of the oxygen sensor 20 when responding to a lean-to-rich transition of the air/fuel ratio relative to the stoichiometric ratio is faster than its time response when responding to a rich-to-lean transition of the air/fuel ratio relative to the stoichiometric ratio. The frequency of the sensor signal of FIG. 6a is the limit cycle frequency of the closed loop control and is generally determined by the engine 10 transport delay and the time constant of the closed loop control. The sensor time response characteristic shown in FIG. 6a in conjunction with conventional sensor signal processing circuits would generally result in the electronic control unit 18 controlling the carburetor 12 so as to supply an air/fuel ratio which is offset from the stoichiometric ratio in the lean direction. For example, if the oxygen sensor signal were utilized in the conventional manner employing a comparator which compares the output of the sensor with a constant reference level which represents the stoichiometric ratio and provides a two-level output signal having one state indicating a rich air/fuel ratio and a second state indicating a lean air/fuel ratio, the two state representation of the air/fuel ratio relative to the stoichiometric ratio would indicate a time relationship between rich and lean wherein the duration of the rich indication would exceed the duration of lean indication even though the actual time duration that the air/fuel ratio is greater than the stoichiometric ratio is equal to the time duration that the air/fuel ratio is less than the stoichiometric ratio. Consequently, the integral term output of the controller when operating in closed loop would adjust the average air/fuel ratio to a value greater than the stoichiometric ratio and until a point is reached where the sensor signal processing circuit output represents the time duration of the rich excursions equalling the time durations of the lean excursions. This result in response to the sensor output voltage of FIG. 6a is illustrated in FIG. 6b. As seen in this figure, the actual air/fuel ratio provided in response to the signal of FIG. 6a is offset in the lean direction from the stoichiometric ratio.

In accord with this invention, the closed loop mode routine 68 of FIG. 4 provides a compensated sensor signal which is independent of the sensor characteristics and particularly the variation of the sensor output signal in response to rich-to-lean and lean-to-rich air/fuel ratio excursions. The resulting adjustment of the carburetor to provide the stoichiometric ratio is therefore independent of this sensor characteristic so that the average air/fuel ratio provided to the engine 10 is the stoichiometric ratio so that maximum conversion efficiency is obtained by the three-way converter 16.

In general, and as illustrated in FIG. 6c, the compensated sensor signal that is provided in response to the actual output signal of the sensor 20 increases at a constant rate that is less than the smallest rate of change of the sensor signal over the sensor life and operating temperature range in response to a change in the oxidizing/reducing condition through the stoichiometric condition when the sensor signal is greater than the compensated sensor signal and that decreases at the constant rate when the sensor signal is less than the compensated sensor signal. Further, the maximum value of the compensated sensor signal is limited to a value less than the maximum output of the sensor signal and the minimum value of the compensated sensor signal is limited to a value that is greater than the lowest value of the sensor signal. This compensated sensor signal is then compared with the reference signal representing a stoichiometric ratio to provide an indication of the sense of deviation of the air/fuel ratio from the stoichiometric ratio to provide the closed loop control signal for adjusting the carburetor 12 to supply the stoichiometric ratio as illustrated in FIG. 6d.

Referring to FIG. 5, the closed loop routine incorporating the principles of this invention is illustrated. The routine is entered at point 72 and the program then proceeds to the decision point 74 where the value of the sensor 20 signal read and stored at step 52 is compared with the value of a compensated sensor signal stored in a ROM designated RAM location. If the sensor signal is greater than the compensated sensor signal, the program proceeds to a decision point 76 where the difference is compared to a calibration value K which, in conjunction with the 100 millisecond interrupt period, determines the slope of the compensated sensor signal. if the difference is greater than the value K indicating that the slope of the sensor signal is greater than the compensated sensor signal by an amount determined by the value of K, the program proceeds to a step 78 where the value of the compensated sensor signal stored in the RAM is increased by the constant K. However, if at step 76 it is determined that the difference between the sensor signal and the compensated sensor signal is less than the constant K, the compensated sensor signal is set equal to the value of the oxygen sensor signal at step 80. From each of the steps 78 and 80, the program proceeds to the step 82 where the value of the compensated sensor signal is limited to the calibration constant $K_{HI}$ which is less than the value of the sensor signal in response to a rich air/fuel ratio. The steps 76, 78 or 80, and 82 function to provide the compensated signal that increases at a constant rate to the limited value $K_{HI}$ during the time period that the sensor signal is greater than the compensated sensor signal.

If it is determined at step 74 that the compensated sensor signal is greater than the sensor signal, the program proceeds to the decision point 84 where the difference is compared to the calibration constant K previously described. If the difference is greater than the calibration constant K, the program proceeds to the step 86 where the compensated sensor signal value stored in the RAM is decreased by the value K. However, if it is determined at step 84 that the difference between the sensor signal and the compensated sensor signal is less than the value K, the compensated sensor signal is set equal to the oxygen sensor signal at step 88. From each of the steps 86 and 88, the program proceeds to the step 90 where the minimum value of the compensated sensor signal is limited to a calibration constant $K_{LO}$. The computer program steps 84, 86 or 88 and 90 function to provide the compensated sensor signal decreasing at a constant rate to the value $K_{LO}$ during the time period that the sensor signal is less than the compensated sensor signal. The resulting compensated sensor signal and its relationship to the sensor signal is illustrated in the FIG. 6c.

From steps 82 and 90, the program proceeds to a step 92 where the condition of a rich-lean flag in the microprocessor 24 is saved in a ROM designated RAM location. The condition of this flag represents the rich or lean state of the air/fuel ratio during the prior 100 millisecond interrupt period.

From step 92, the program proceeds to a decision point 94 where the value of the compensated sensor signal is compared with a reference voltage $V_{ref}$ representing a stoichiometric air/fuel ratio. If the compensated sensor voltage is greater than this reference voltage, representing a rich air/fuel ratio, the program proceeds to a step 96 where the rich-lean flag in the microprocessor 24 is set to indicate a rich air/fuel ratio. If the compensated sensor signal is less than the reference voltage, the program proceeds from step 94 to the step 98 where the rich-lean flag is reset to indicate a lean air/fuel ratio.

From each of the steps 96 and 98, the program proceeds to the decision point 100 where the present rich or lean state of the air/fuel ratio relative to the stoichiometric ratio represented by the state of the rich-lean flag in the microprocessor 24 is compared with the state of the rich-lean flag saved at step 92 and representing the rich or lean state of the air/fuel ratio during the prior 100 millisecond interrupt period. If the comparison indicates a rich-lean transition has not occurred, only an integral term adjustment is provided to the stored carburetor control pulse width and the program cycle proceeds to a decision point 102. If a lean-to-rich transition is detected, the program proceeds to a step 104 wherein a predetermined proportional term value stored in the ROM is added to the carburetor control pulse width value stored in the RAM to effect a proportional step increase in the duty cycle of the carburetor control signal. If a rich-to-lean transition is detected, the program proceeds to a step 106 wherein a predetermined proportional term value stored in the ROM is subtracted from the carburetor control pulse width stored in the RAM to effect a proportional step decrease in the duty cycle of the carburetor control signal.

From either of the steps 104 and 106, the program cycle proceeds to the decision point 102 where the rich or lean state or the air/fuel ratio represented by the rich-lean flag in the microprocessor 24 is sensed. If the rich-lean flag is set representing a rich air/fuel ratio, the program cycle proceeds to a step 108 where a predetermined integral step is added to the carburetor control pulse width value stored in the RAM. If the rich-lean flag is reset indicating the air/fuel ratio is lean relative to the stoichiometric ratio, a predetermined integral step is subtracted at a step 110 from the carburetor control pulse width stored in the RAM. From each of the steps 108 and 110 the program exits the closed loop mode routine at step 112 and proceeds to the step 70 previously described.

During continued closed loop operation of the electronic control unit 18, the carburetor control duty cycle varies in direction tending to restore the stoichiometric air/fuel ratio in response to the compensated sensor signal. The resulting carburetor control duty cycle is illustrated in the FIG. 6d. As seen in this figure, the average of the limit cycle carburetor control duty cycle provided to adjust the air/fuel ratio controls the carburetor to a stoichiometric air/fuel ratio as opposed to the offset air/fuel ratio illustrated in FIG. 6b in response to the actual oxygen sensor signal.

As can be seen from the foregoing, the closed loop duty cycle is provided in response to a compensated sensor signal that is insensitive to the variations in the time response of the oxygen sensor to transitions in the air/fuel ratio between rich and lean values. The provision of the compensated sensor signal that is symmetrical about a single reference value with which it is compared provides for the control of the air/fuel ratio to the stoichiometric ratio without any offset thereby maximizing the three-way conversion efficiency of the three-way converter 16.

The foregoing description of a preferred embodiment for the purpose of illustrating the invention is not to be considered as limiting or restricting the invention, since many modifications may be made by one skilled in the art without departing from the scope of the invention.

The embodiments of the invention in which an exclusive property or privilege is claimed are defined as follows:

1. A fuel control system for an internal combustion engine having means defining an exhaust passage into which spent combustion gases are discharged, comprising, in combination:

a sensor responsive to the oxidizing/reducing conditions in the exhaust passage effective to generate a sensor signal varying between high and low values when the oxidizing/reducing condition of the exhaust gases varies through a stoichiometric condition, the time response of the sensor signal to changing oxidizing/reducing conditions in one direction through the stoichiometric condition varying from its time response to changing oxidizing/reducing conditions in the opposite direction through the stoichiometric condition and varying with sensor aging and operating temperature;

means responsive to the sensor signal effective to generate a compensated sensor signal (A) increasing at a constant rate less than the smallest rate of change of the sensor signal over the sensor life and operating temperature range in response to a change in the oxidizing/reducing condition through the stoichiometric condition when the sensor signal is greater than the compensated sensor signal and (B) decreasing at the constant rate when the sensor signal is less than the compensated sensor signal;

means effective to limit the maximum value of the compensated sensor signal to a value less than the sensor signal high value and limiting the minimum value of the compensated sensor signal to a value greater than the sensor signal low value;

means effective to compare the compensated sensor signal to a reference value intermediate the limited values of the compensated sensor signal and which represents a desired oxidizing/reducing condition of the exhaust gases and providing an error signal; and means responsive to the error signal effective to adjust the ratio of the air-fuel mixture supplied to the engine in a sense tending to restore the desired oxidizing/reducing condition, the adjustment of the air-fuel ratio being independent of variations of the time response of the sensor signal.

2. The method of generating a compensated sensor signal from the sensor signal provided by a sensor monitoring the oxidizing/reducing condition in the exhaust gases discharged from an internal combustion engine for use in a closed loop air/fuel ratio controller, comprising the steps of:

comparing the value of the sensor signal with the value of the compensated sensor signal;

increasing the value of the compensated sensor signal at a constant rate less than the smallest rate of change of the sensor signal in response to a change in the oxidizing/reducing condition through the stoichiometric condition when the value of the sensor signal is greater than the value of the compensated sensor signal;

decreasing the value of the compensated sensor signal at the constant rate when the value of the sensor signal is less than the value of the compensated sensor signal; and limiting the compensated sensor signal to values between a maximum value less than the maximum sensor signal value and a minimum value greater than the minimum sensor signal value, the compensated sensor signal being independent of differences in the time response of the sensor signal in response to changes in the oxidizing/reducing conditions through the stoichiometric condition.

* * * * *